United States Patent [19]

Andersen et al.

[11] Patent Number: 5,017,493
[45] Date of Patent: May 21, 1991

[54] DNA SEQUENCE

[75] Inventors: Henrik D. Andersen, Charlottenlund, Denmark; Hans H. M. Dahl, Parville, Australia; Thorkild Christensen, Allerod, Denmark

[73] Assignee: Nordisk Gentofte A/S, Gentofte, Denmark

[21] Appl. No.: 470,396

[22] Filed: Jan. 25, 1990

Related U.S. Application Data

[63] Continuation of Ser. No. 3,380, filed as PCT DK86/00030 on Apr. 3, 1986, published as WO86/05805, Oct. 9, 1986, abandoned.

[30] Foreign Application Priority Data

Apr. 3, 1985 [DK] Denmark .................... 1525/85

[51] Int. Cl.$^5$ ............... C12N 15/00; C12N 15/03; C12N 15/11; C12N 15/67
[52] U.S. Cl. .................... 435/252.3; 435/172.3; 435/320.1; 530/27; 935/29; 935/44; 935/45; 935/72
[58] Field of Search ............... 435/91, 172.1, 172.3, 435/320, 252.3–252.35, 69.1, 71.2; 536/27; 935/29, 44, 45, 72–75

[56] References Cited

U.S. PATENT DOCUMENTS 4,686,191 8/1987 Itoh et al. ..................... 435/320

FOREIGN PATENT DOCUMENTS

| | | | |
|---|---|---|---|
| 0115613 | 8/1984 | European Pat. Off. | |
| 0134673 | 3/1985 | European Pat. Off. | 435/172.3 |
| 0134589 | 4/1985 | European Pat. Off. | 435/172.3 |
| 8605805 | 10/1985 | World Int. Prop. O. | 435/172.3 |

OTHER PUBLICATIONS

Yansura et al; Proc. Natl. Acad. Sci. U.S.A., 81: 439 (1984).
Jay et al; Nucleic Acids Res. 10: 6319 (1982).
Backman et al; Cell 13: 65–71 (1978).
DeBoer et al; in *Promoters*, Rodriguez et al. (ed.), 1982, Praeger Publishers, New York, pp. 462–481.
Shepard et al; DNA, vol. 1, No. 2, pp. 125–131 (1982).

*Primary Examiner*—James Martinell
*Attorney, Agent, or Firm*—Ladas & Parry

[57] ABSTRACT

A DNA sequence containing a ribosome binding site with a SD sequence AGGA and a start codon ATG, comprising a nucleotide sequence having the formula $Y_1 \ldots Y_m ZVAGGA\ X_1, X_2 \ldots X_n ATG$ wherein $Y_1 \ldots Y_m$ represents a promoter with one or more restriction enzyme sites, m being an integer corresponding to the number of base pairs in the promoter, each X, Y, Z and V is A, T, C or G; n is 9 to 13, and the sequence $X_1 \ldots X_n$ cannot contain a start codon.

7 Claims, 1 Drawing Sheet

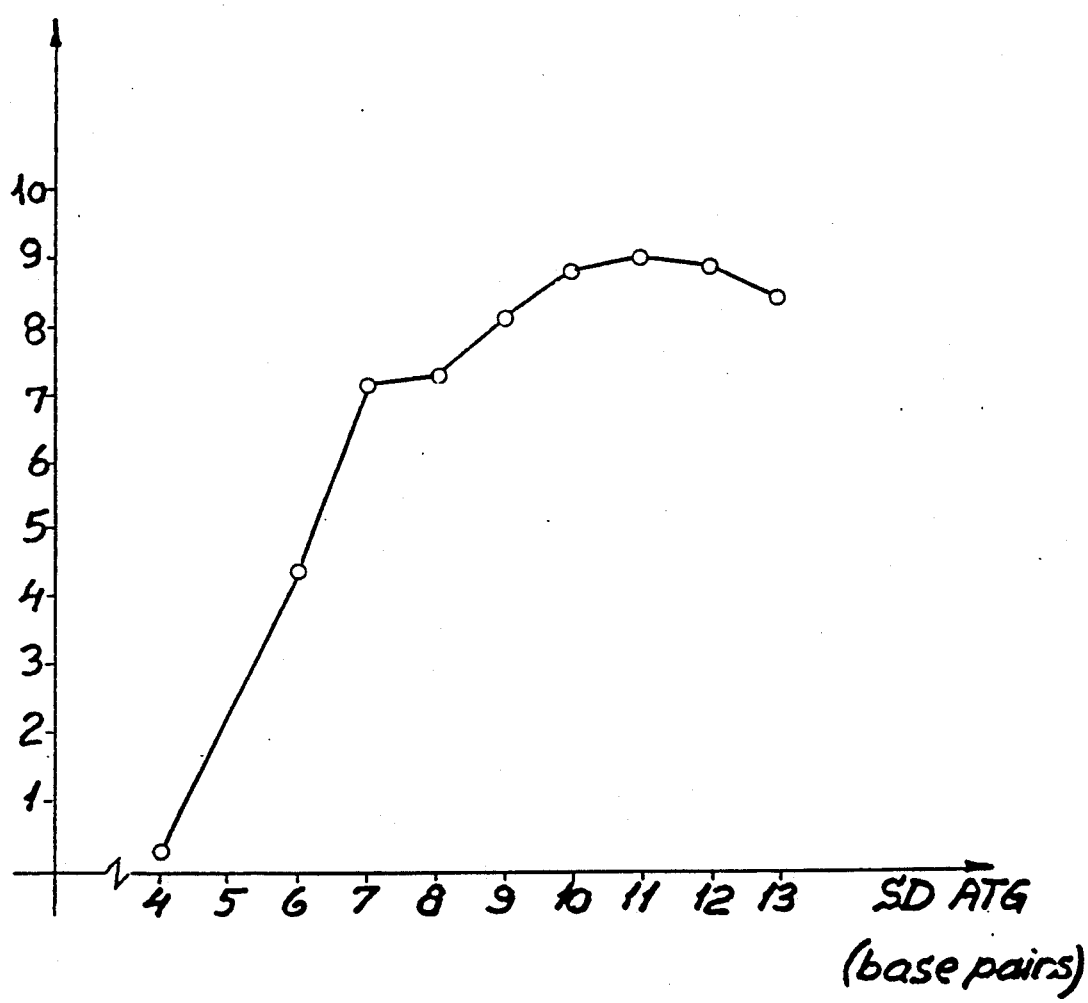

DNA SEQUENCE

This is a continuation of copending application Ser. No. 07/003,380 filed on Jan. 20, 1987, now abandoned and International Application PCT/DK86/0030 filed on April 3, 1986 and which designated the U.S.

The present invention concerns a DNA sequence intended for introduction into a plasmid or another replicable cloning medium which codes for a desired polypeptide.

In biosynthetic methods of producing desired polypeptides or proteins, it is known to use microorganisms which are transformed with a plasmid or a similar expression vector which codes for the desired polypeptide or protein, so that, when cultivated on a suitable substrate, the microorganism produces the desired polypeptide or protein, which may then be isolated from the fermentation liquid in a manner known per se. A microorganism suitable for this purpose is $E.$ $coli.$ The plasmid or a similar expression vector may be produced synthetically or semi-synthetically, e.g. from a plasmid which is functional in the microorganism concerned and which is cleaved enzymatically, and then the DNA sequence coding for the desired polypeptide is introduced into the plasmid by known recombinant procedures.

In addition to the DNA sequence coding for the desired polypeptide, a functional plasmid must also contain a promotor region to which the RNA polymerase may attach and initiate the transcription of the coding DNA sequence to form mRNA, which is translated to the desired polypeptide by translation on the ribosomes.

The promotor region is followed by a ribosome binding site, which is often called a Shine Dalgarno region, which the nucleotide sequence AGGA.

To enable formation of the plasmid by known recombinant procedures, the promotor region should include restriction enzyme cleavage sites allowing enzymatic cleavage and introduction of the actual DNA sequences. Further, a gene is generally introduced, making the microorganism resistant to a specific antibiotic. Examples of this are ampicillin resistant or streptomycin resistant genes. The resistant, transformed microorganisms may be isolated from the untransformed microorganisms by means of the antibiotic substances in question.

To obtain a high yield or production of the desired protein it is important that the following conditions are met:

1. The polymerase binding site in the promotor must have a structure which promotes optimum binding of the RNA polymerase,
2. The ribosome binding site must have an optimum structure enabling formation of complementary mRNA which attaches effectively to the ribosome.

An object of the present invention is to provide a DNA sequence which, when introduced into a replicable cloning medium codes for the ribosome binding site which ensures good binding of the mRNA to the ribosome and thus effective translation to provide the desired protein.

Another object of the invention is to change the composition of the ribosome binding site in plasmids or other transfer vectors used for expression of a desired protein to improve the yield of the translation.

Examinations have previously been made of the DNA structure in the ribosome binding site in various microorganisms (Nucleic Acids Res. (1982) 10, 6319–6329), and the influence of various changes of the structure on the translation effect has been determined.

The ribosome binding site comprises an SD sequence which is often composed of the nucleotides AGGA. Between this sequence and the start codon ATG coding for methionine there is a plurality of nucleotides or a spacer region whose composition and size influence the efficiency of the translation.

BRIEF DESCRIPTION OF THE DRAWING

The FIGURE illustrates the expression of Met-hGH as a function of the number of base pairs between the SD sequence and ATG.

DESCRIPTION OF THE PREFERRED EMBODIMENTS

The present invention is based on an examination of the importance of the composition and size of this spacer region. Thus, according to the invention it has been found that optimum translation is obtained if the ribosome binding site with associated SD sequence and start codon has the formula $Y_1 \ldots Y_m ZVAGGA\ X_1, X_2 \ldots X_n ATG$ wherein $Y_1 \ldots Y_m$ represents a promoter with one or more restriction enzyme sites, m being an integer corresponding to the number of base pairs in the promoter; each Y, Z, V and X is A, T, C or G; n is 9 to 13, and wherein the sequence $X_1 \ldots X_n$ cannot contain a start codon. According to preferred embodiments of the invention, the subject DNA sequence has a composition as stated in each of the dependent claims providing for optimum translation rate and yield.

Such an effect could not be predicted on the basis of previous studies, such as the above-mentioned report in Nucleic Acids Res. (1982).

The novel DNA sequence of the invention together with the gene to be expressed may be introduced by recombinant procedures known per se into the ordinary replicable cloning media, such as a plasmid, which may be transferred in a known manner to a microorganism producing the desired protein by cultivation on a substrate.

The subject DNA sequence may be used in connection with any replicable cloning medium, no matter which protein it is desired to produce. Thus the sequence may be used in connection with plasmids coding for insulin, human growth hormone, interferon or any other desired polypeptide or protein, and in all cases the yield obtained by the production of these proteins is surprisingly improved.

It has no importance for the effectiveness of the ribosome binding site which composition the replicable cloning medium otherwise has. If it is desired to introduce an antibiotic-resistant gene into the cloning medium, its type may thus be selected freely to obtain effective separation of the transformed microorganism from untransformed cells.

The composition of the promotor is selected with a view to the achievement of optimum transcription. Examples of suitable promotors are the following DNA sequences:

```
BamHI                       SacI                                                      (A)
GGATCCTGTTGACAATTAATCATAGAGCTCGTATAATGTG

EcoRI
GAATTCTGCAGATCTAACAATTAAGCTT
         BglII        HindIII

EcoRI                              SacI                                               (B)
CGAATTCGATCCTGTTGACAATTAATCATAGAGCTCGTATAATGTGGAATTGTG—

BglII          HindIII
CAGATCTAACAATTAAGCTT
```

Only the +strand is shown in these and subsequent formulae, unless otherwise stated.

The invention will be illustrated more fully below by means of some working examples.

EXAMPLE 1

Comparison of the SD sequence AGGA and the SD sequence TAAGGAGGT

A plasmid expressing Met-hGH under control of a synthetic promotor was constructed as described below.

A fragment containing the Met-hGH coding sequence and the translation stop signal as well as two bases 5' and 6 untranslated bases 3' for the hCH sequence was cut out of the plasmid pHD59-10 with the restriction enzymes Cla I/Sma I and isolated by gel electrophoresis.

A synthetic DNA fragment was constructed, containing i.a. EcoRI site, RNA polymerase binding site, ribosome binding centre and Cla I site.

This promotor SP3 has the nucleotide sequence:

```
CGAATTCGATCCTGTTGACAATTAATCATAGAGCTCGTA
TAATGTGGAATTGTGCAGATCTAACAATTAAGCTT
AGGATCTAGAAATCGAT
```

It is known from the literature that a transcription terminator introduced after the translation stop signal in the gene is to be expressed is an advantage since the terminator when stopping the transcription prevents reading of and thus interference from other genes, regulation regions and the start region for DNA replication. Such a terminator may e.g. be the terminator from the phage fd (R. Gentz. et al: Proc. Natl. Acad. Sci. USA, Vol. 78, No. 8, p. 4936-4940, 1981).

An about 375 bp HIND III fragment containing the fd terminator was isolated and made blunt ended by means of Knenow polymerase +dNTP. The fragment was then cut with the restriction enzyme BamHI, and an about 365 bp fragment with a blunt 5' end and a BamHI overhand at the 3' end was isolated.

The above-mentioned three isolated fragments were then ligated into the plasmid pAT153, which had been cut with EcoRI/BamHI. The hGH production was hereby subjected to the synthetic promotor. The plasmid thus constructed was called pHD67SP3.

The ligation mixture was transformed in a known manner into *E. coli* MC1061. The clone pHD6711SP3 was selected and cultivated in 10 ml LB medium admixed with ampicillin. The cells were harvested after 8 hours' growth, lysed by ultrasonic treatment and analysed for content of hGH immuno-reacting peptides by means of ELISA (B. Dinesen and H. Dalbøge Andersen: Analytica Chimica Acta, 163 (1984) 119-125) and RIA.

A comparison of the RIA and ELISA results between hypophyseal hGH Nanormon ®, and the Met-hGH produced by cultivation of HD67-11 SP3 showed that they diluted in parallel. HPLC was performed on cell lysate from HD6711Sp3, partly as pure cell lysate, partly as cell lysate admixed with Nanormon ®. A peak characteristic of hGH resulted in both cases. The first 15 amino acids were determined by automatic Edman degradation (P. Edman and G. Begg: Eur. J. Biochem. 1(1967), p. 80-91) after purification of the product and were found to be identical with the amino acid sequence for Met-hGH.

The biological activity of the produced bacterial Met-hGH was examined by a tibia test and was found to correspond to the activity of Nanormon ®.

To examine the effect of an amended SD sequence, the plasmid pHD6711SP3 was cut with the restriction enzymes HInd III/Cla, enabling removal of its original SD region. Instead, a synthetic DNA fragment with the following sequence was introduced:

```
AGCTTAAGGAGGTTAAAAT
    ATTCCTCCAATTTTAGC
``` to obtain the plasmid pHD6711SP14.

The obtained plasmid transformed into *E. coli* MC1061 in a known manner. The clone pMD6711SP14-1 was selected and cultivated in 10 ml LB medium admixed with ampicillin. The cells were harvested after 8 hours' growth, lysed by ultrasonic treatment and analysed as described for HD6711SP3.

The expression levels of HD6711SP3 and HD6711SP14-1 were measured, table I and found to be about 10 times higher for HD67115P14 compared with HD6711SP3.

TABLE 1

| Promotor | SD-ATG | Sequence | mg hGH/l OD1 |
| --- | --- | --- | --- |
| SP3 | 11 | AGCTTAGGATCTAGAAATCGATG | 0.8 |
| SP14-1 | 11 | AGCTTAAGGAGGTTAAAATCGATG | 10 |

The promotor Shine Dalgarno regions were determined by DNA sequence analysis as a control.

EXAMPLE 2

Examination of the influence of the SD-ATG distance on the expression of Met-hGH The plasmid pHD6711SP14 was used as a starting material in an examination of what is the optimum distance between ACGA and ATG as the SD region was changed by introduction of synthetic DNA fragments of different length, table II, but so that the SD sequence TAAGGAGGT remained unchanged. The plasmid HD6711SP14 was cut with the restriction enzymes Hind III/Cla I, and then the plasmid fragment was purified on a gel.

Eight synthetic DNA fragments were then ligated as shown in Table II into the plasmid to obtain the shown structures.

After transformation into *E. coli* MC1061 and selection of the clones, these were cultivated in LB admixed with ampicillin. The cells were harvested after 16 hours' growth, lysed by ultrasonic treatment and analysed for content of hGH by means of ELISA. As will be seen from Table II and FIG. 1, the greatest expression of Met-hGH is obtained then the SD-ATG distance is between 10 and 12 bases.

All structures were DNA sequence determined and found to be as expected.

TABLE II

| Promotor | SD-ATG | Sequence | mg/hGH/1 OD1 |
|---|---|---|---|
| SP6-5 | 13 | AGCTTAAGGAGGTTATAAATTCGATG | 8.4 |
| SP5-10 | 12 | AGCTTAAGGAGGTTATAAATCGATG | 8.9 |
| SP7-1 | 11 | AGCTTAAGGAGGTTCCTTACGATG | 9.0 |
| SP14-1 | 11 | AGCTTAAGGAGGTTAAAATCGATG | 8.9 |
| SP8-5 | 10 | AGCTTAAGGAGGTTATAACGATG | 8.8 |
| SP9-1 | 9 | AGCTTAAGGAGGTTATACGATG | 8.0 |
| SP13-2 | 9 | AGCTTAAGGAGGTTAATCGATG | 7.7 |
| SP10-4 | 8 | AGCTTAAGGAGGTTATCGATG | 7.3 |
| SP11-6 | 6 | AGCTTAAGGAGGTTCGATG | 4.4 |

This data is shown in the FIGURE.

EXAMPLE 3

Expression of MAE-hGH MAEAE-hGH and MAEE-hGH

To examine whether the promotors might also be used for expression of other genes than Met-hGH, the genes for met-ala-glu-hGH, met-ala-glu-ala-glu-hGH and met-ala-glu-glu-hGM were introduced into a plasmid containing the promotor SPI3, using known DNA technological methods.

After transformation of the plasmids into *E. coli* MC1061, the clones were cultivated and lysed as described in example 2, and the hGh production was measured by ELISA. The found yields are stated in table III.

TABLE III

| Clone | mg hGH/1 OD1 |
|---|---|
| MAE-hGH | 10 |
| MAEAE-hGH | 8 |
| MAEE-hGH | 8.5 |

What is claimed:

1. A recombinant sequence containing a ribosome binding site with the SD sequence AGGA and the start codon ATG, comprising a nucleotide sequence whose +strand has the formula:

$$AGCTTAAGGAGGTX_1X_2\ldots X_nCGATG$$

wherein X is A, C or T, n is 5–8.

2. A DNA sequence according to claim 1, containing the sequence AGCTTAAGGAGGTTATAAATTCGATG.

3. A DNA sequence according to claim 1, containing the sequence AGCTTAAGGAGGTTCCTTACGATG.

4. A DNA sequence according to claim 1, containing the sequence AGCTTAAGGAGGTTAAAATCGATG.

5. A DNA sequence according to claim 1, containing the sequence AGCTTAAGGAGGTTATAACGATG.

6. A replicable cloning vector, containing the DNA sequence stated in claim 1 and a gene coding for a desired protein, optionally followed by a transcription stop signal.

7. A bacterium containing the replicable cloning vector stated in claim 1.

* * * * *